United States Patent

Mulhollan et al.

Patent Number: 4,614,187
Date of Patent: Sep. 30, 1986

[54] NEEDLE EXTRACTOR

[76] Inventors: James S. Mulhollan, 3401 Foxcroft Rd., Little Rock, Ark. 72207; Lionel Starr, 8806 Patricia Lynn, Sherwood, Ark. 72116

[21] Appl. No.: 595,819

[22] Filed: Apr. 2, 1984

[51] Int. Cl.$^4$ .............................................. A61B 17/50
[52] U.S. Cl. ............................ 128/303 R; 128/92 EC; 128/340
[58] Field of Search ............. 128/92 EC, 92 ED, 340, 128/346, 303 R, 356

[56] References Cited

U.S. PATENT DOCUMENTS

| | | | |
|---|---|---|---|
| 1,539,221 | 5/1925 | Tennant | 128/340 X |
| 1,934,818 | 11/1933 | Richter | 128/320 |
| 2,396,179 | 3/1946 | Karle | 128/340 |
| 2,516,492 | 7/1950 | Turkel | 128/751 |

OTHER PUBLICATIONS

"Suture of New and Old Peripheral Meniscus Tears", 2/83, Hamberg, Gilquist and Lysholm.
"Arthroscopic Meniscal Repair", Clancy, Jr., and Graf.
"Arthroscopic Repair . . . The Next Step", Acufex Micro Surgical, Inc.
"Mechanical Description for Acufex Meniscal Stitcher", Acufex Micro Surgical, Inc.

Primary Examiner—Michael H. Thaler
Attorney, Agent, or Firm—Hill, Van Santen, Steadman & Simpson

[57] ABSTRACT

A needle extractor is provided for removing elongated surgical needles from within a patient body which comprises a ratchet activated rod member insertable though a cannula and having a hole for grasping and pulling the needle. The cannula is provided with a slim abutting ring to prevent movement of the cannula tip during the extraction process.

5 Claims, 8 Drawing Figures

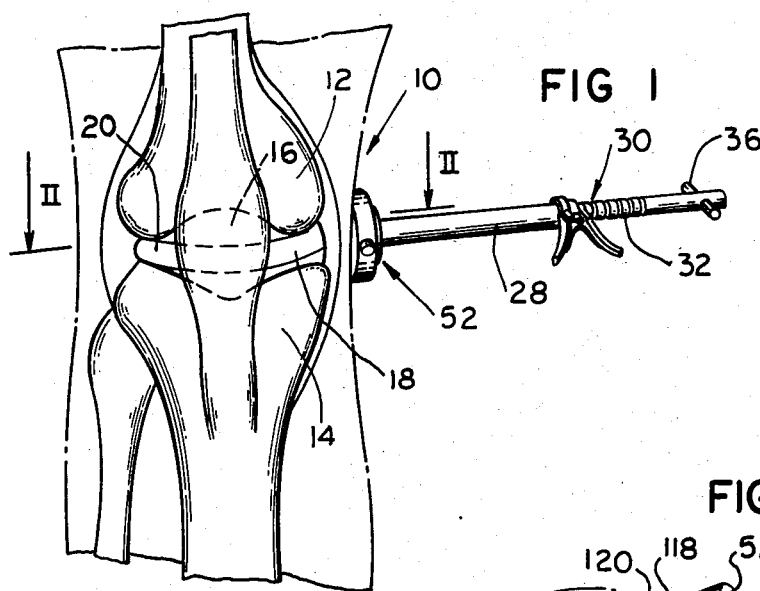
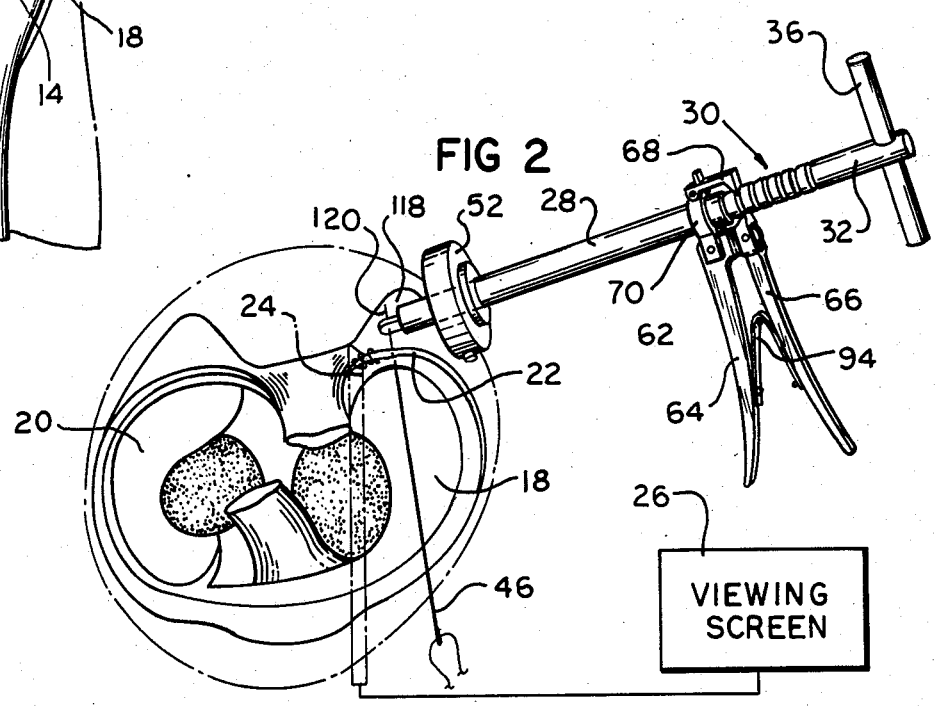
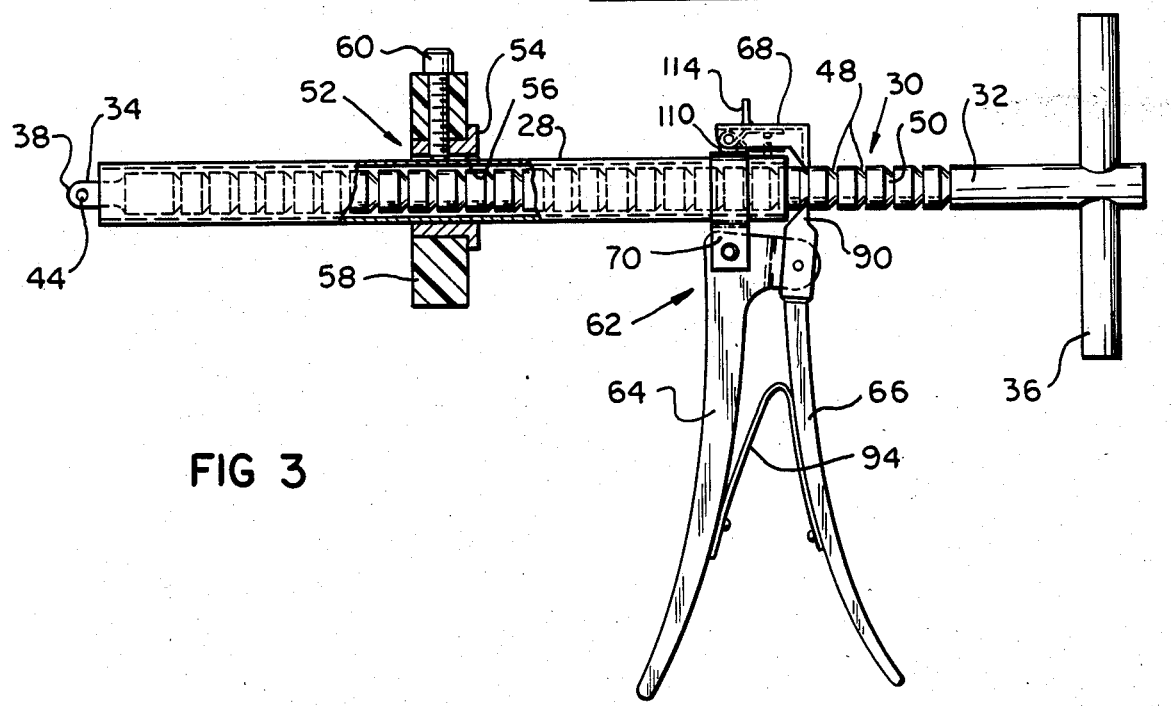

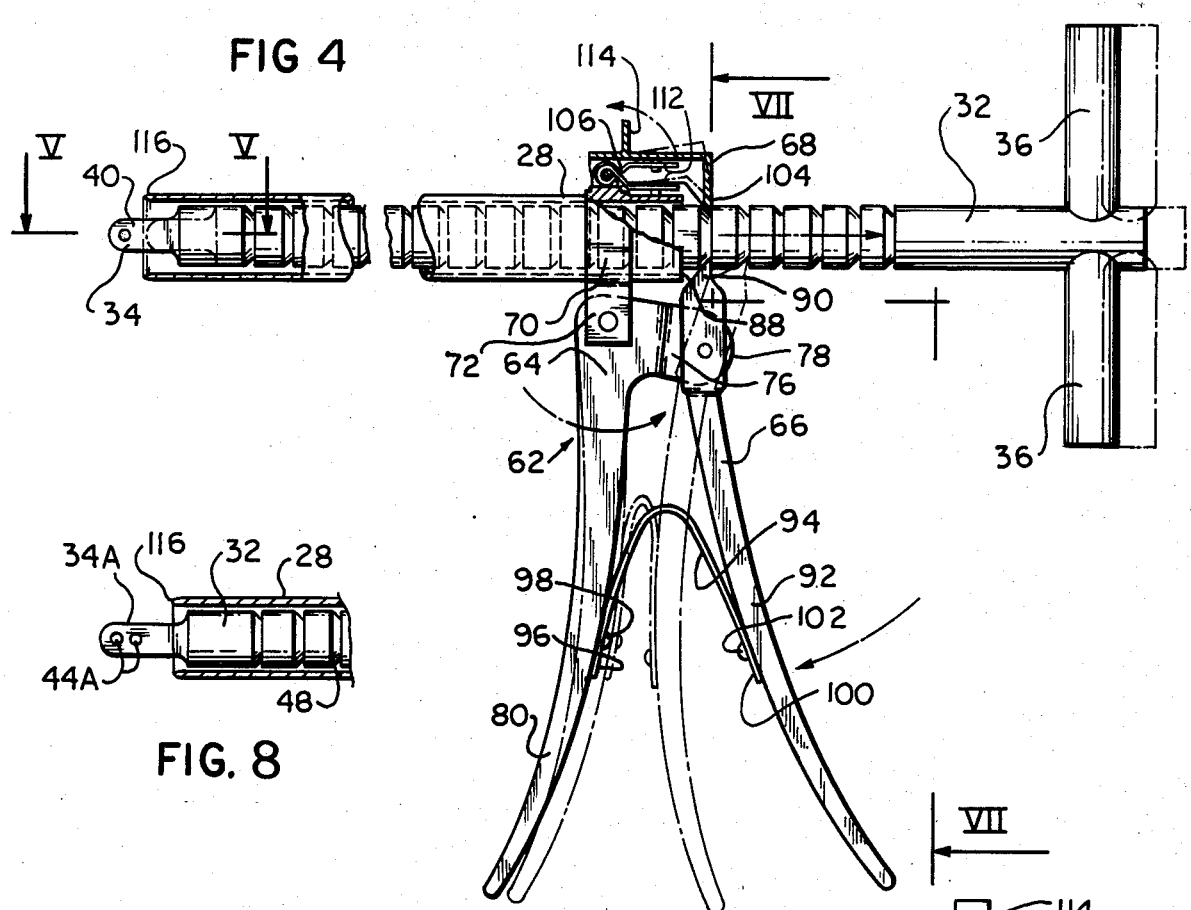
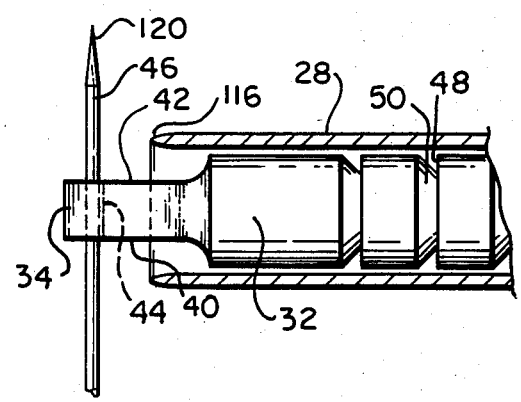
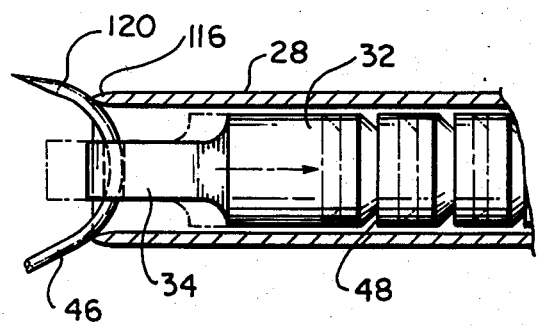
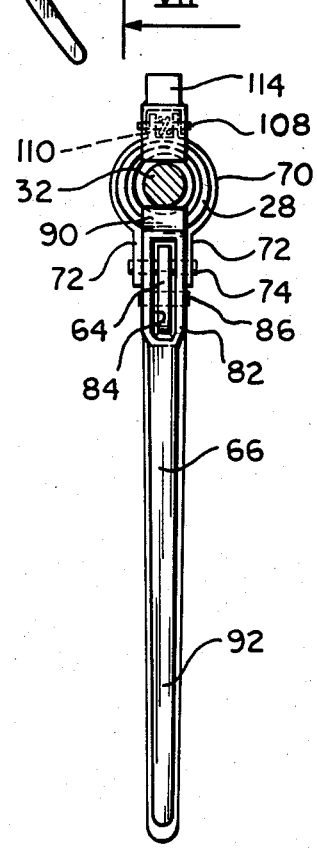

NEEDLE EXTRACTOR

BACKGROUND OF THE INVENTION

1. Field of the Invention

This invention relates to surgical instruments and more particularly to a device of grasping and extracting a needle used for placing sutures within a body of tissue or cartilage such as the body of a human being or of an animal.

2. Description of the Prior Art

Many surgical procedures are currently being performed where it is necessary to make a large opening to expose the area of, for instance, a human body that requires surgical repair. This is true even though there are instruments available which allow the viewing of certain areas which have limited accessibility. For example, arthroscopes are available to permit viewing of a human knee joint through a puncture wound without exposing the entire joint of the knee by cutting through the skin in that area.

These viewing instruments can be used to detect, among other things, surgically repairable tears within the cartilage of the knee. Shaving instruments exist which allow parts of the damaged cartilage to be shaved off and removed from the knee joint through a cannula or tube without requiring that the knee be opened. However, prior to this time it has been necessary to open the knee to sew the tear in the cartilage.

When an area of the body is cut into to expose an interior portion thereof, that process involves some morbidity which increases as more muscle layers, ligaments and other tissues are cut and separated. This morbidity, or time and discomfort associated with recovery and chance of complications, would be greatly reduced if the required surgery were performed without making a large incision, cutting and separating various tissues, and exposing a large portion of the interior of the body.

A device has been provided to introduce one or two needles carrying suture material into a relatively inaccessible location percutaneously through a cannula by using one or two 25 cm. long needles to pass entirely through the knee joint. Although such an approach may work in some cases, there are neurovascular structures directly behind the menisci in the knee joint which could be jeopardized by the passage of the needles through that area.

SUMMARY OF THE INVENTION

The invention provides for a device and method of performing surgical repair requiring stitches on areas of the interior of the body having limited access through a cannula. This is done percutaneously, or through a puncture wound in the skin, without requiring a large incision for exposing the interior of the body. The device of the present invention comprises a needle extractor which is small enough to be inserted through a cannula, yet sturdy enough to grasp, bend and extract an elongated surgical needle previously inserted through the joint tissue. The device is operable to grasp the needle, bend it so it can be extracted through the cannula, and complete the extraction process in a smooth, yet forceful manner. Also, the needle carrier has the ability to grasp the needle very securely during passage through the cannula.

The procedure for using the device embodying the principles of the invention begins with introducing a tube into the knee or other area to be worked on by means of a fitted cannula that is rounded on the tip to avoid injury to neurovascular and other structures. Unique about this particular tube is that it has a ring that can be moved down adjacent to the skin of the patient and fixed in that position. By using the ring, a ratchet mechanism has something to push against so that the tip of the tube does not move relative to the needle location within the knee joint as the needle is pulled around an angle out through the tube.

The surgical needle is grasped by manipulating a rod portion of the needle extractor such that the needle passed through a hole in the rod. The ratchet mechanism withdraws the rod causing the needle to be bent around the end of the tube and pulled out through the tube and gradually out of the joint. The ratchet allows for the pulling to occur under control and slowly.

One or two needles can be carried through the tube in the fashion described with one ratchet mechanism. If a single needle is passed, then the trailing end of the suture material is caught within the knee by a suture manipulator, pulled until there is slack, and then passed into the postero-medial compartment through the intercondylar notch. A grasping instrument can then be introduced through the tube posterial-medially, and the suture caught and pulled out so that both ends of the suture are out through the tube posterial-medially.

Thus, the present invention provides the advantage of being able to make repairs requiring stitches within the interior of a body in a relatively inaccessible area through a puncture wound without making a large incision and allowing for extraction of the surgical needle without jeopardizing the neurovascular or other structures adjacent the area being stitched.

BRIEF DESCRIPTION OF THE DRAWINGS

FIG. 1 is a front view of the environment of a human knee showing the joint structure in full lines and the outline of a leg in phantom and showing the needle extractor device in place.

FIG. 2 is a top sectional view though the knee showing the placement of the needle extractor device in operation, taken generally along the line II—II of FIG. 1.

FIG. 3 is a detailed partial cross-sectional view of the needle extractor device inside a cannula.

FIG. 4 is a detailed partial cross-sectional view of the device shown in FIG. 3 showing the movement and operation of the device.

FIG. 5 is a partial top view of the needle extractor device showing the head portion grasping a needle.

FIG. 6 is a partial top view of the needle extractor device showing movement of the head portion and bending of the needle.

FIG. 7 is a partial sectional view of the body of the needle extractor taken generally along the line VII—VII of FIG. 4.

FIG. 8 is a partial side sectional view of an alternate embodiment of the head portion.

DESCRIPTION OF THE PREFERRED EMBODIMENTS

Although the principles of the present invention are applicable to any device suitable in surgical procedures whether performed on humans or animals, a particular utility is effected in human knee surgery where the problems of surgery are particularly acute. Accordingly, as an illustrative exemplification of our invention in FIG. 1 there is shown a human knee joint generally at 10 which provides an environment in which the present invention is especially useful. Within the knee joint 10 there is shown the femur bone 12, the tibia bone 14, the patella or knee cap 16 and the medial meniscus 18 and lateral meniscus 20. The menisci 18, 20 are cartilage structures in contact with both the femur 12 and tibia 14. As seen in FIG. 2, the menisci are crescent shaped with a central opening area. Certain injuries to the knee cause tears to the menisci such as that shown in 22 in FIG. 2.

Arthroscopes are available which have a light and optics probe, as shown at 24, which can be inserted through a puncture wound for viewing the interior portion of the knee joint 10 through a viewing lens or screen shown schematically at 26 (FIG. 2). The arthroscope permits the physician or surgeon to see the tear 22 without surgically opening the knee to expose that portion of the joint.

A hollow cannula or tube 28 can be inserted through the skin around the knee joint to a position proximate to the tear 22 in the miniscus 18. Various instruments can be inserted through this cannula 28 to perform various surgical tasks. The present invention provides for an instrument which can be inserted through this cannula 28 to grasp and extract one or more needles that have set a stitch in the meniscus so that the tear 22 can be sewn shut to assist in the healing process without opening the knee to expose this portion of the knee joint. Such a procedure is greatly advantageous over previous methods of knee surgery in that healing time is drastically reduced to days instead of weeks. Additionally, grasping and extracting the needle through a cannula, which has been placed in an area avoiding tissue and other structures which may be injured, is greatly beneficial over passing the needles all the way through the knee joint for extraction.

A needle extractor 30 is shown in each of the figures and is comprised of a rod member 32 having a head portion 34 at one end and a perpendicularly arranged handle member 36 at an opposite end. The rod 32 has an outer diameter sufficiently lesser than the inner diameter of the cannula bore to afford a clearance to allow it to move loosely in the cannula 28. A typical rod diameter would be about 5 mm.

The head portion 34 of the rod 32 has a rounded end 38 and has a rectangular cross section. The head portion 34 has a pair of opposed flat faces 40, 42 (FIG. 5) with a hole 44 passing therethrough. The hole 44 is sized to accomodate a surgical needle 46 in a loose fit.

The shank of the rod 32 contains a plurality of equally spaced grooves 48 extending a significant portion of the length of the rod 32. The grooves 48 may be provided with an angled wall 50 in the form of a truncated cone with the base end disposed toward the head portion 34 of the rod 32.

Selectively movably securable to the cannula is a ring member 52 comprising a bushing 54 having an interior passage 56 adapted to loosely engage the cannula 28 and an outer ring member 58 secured to the bushing 54 by a friction fit. Securing means 60 such as a set screw passes radially through the outer ring member 58 and the bushing 54 to engage the outer wall of the cannula 28 to prevent rotational or axial movement of the ring member 52 relative to the cannula 28. The ring member 52 can be selectively positioned at any desirable point along the length of the cannula 28.

Secured to an end of the cannula 28 is a ratchet mechanism 62 comprising a crank member 64, a lever member 66 and a ratchet dog member 68. A strap or bracket member 70 is secured to the cannula 28 and has a pair of ears 72 extending outwardly from the cannula 28. A portion of the crank member 64 is positioned between the ears 72 and is held in position by a pivot pin 74 extending through the ears 72 and the crank member 64. A short arm portion 76 of the crank member 64 extends axially relative to the cannula 28 and terminates in a rounded end 78. An elongated arm member 80 of the crank member 64 extends radially outwardly from the cannula 28 in a gently curving manner in the axial direction.

The lever member 66 has an enlarged first end 82 with a central opening 84 therethrough to receive the rounded end 78 of the arm 76. A second pivot pin 86 extends through the enlarged end 82 and the rounded end 78 to hold the lever member 66 and crank member 64 in a relatively fixed, yet pivotable relationship. The length of the arm 76 is sufficient to hold the enlarged end 82 of the lever member 66 beyond an end 88 of the cannula 28. The enlarged end 82 terminates in a tooth type projection 90 having a pointed end with a lateral expanse. The lever member 66 has a radially outwardly extending arm portion 92 extending outwardly from the enlarged end 82 substantially parallel to the elongated arm 80 of the crank member 64 but having a gentle curve in an axial direction away from the curve of the crank arm 80.

A leaf type spring 94 is secured adjacent a first end 96 to the crank arm 80 by an appropriate fastening means 98 and at adjacent a second end 100 to the lever arm 92 by an appropriate fastening means 102. The lever member 66 is pivotable about pivot pin 86 relative to the crank member 64, however, the spring member 94 biases the two arms apart.

The ratchet dog member 68 is secured to the cannula 28 radially opposite the crank member 64 and lever member 66 and comprises a spring mounted dog member having a tooth like projection 104 projecting beyond the end 88 of the cannula 28 in a radially inwardly direction. A spring member 106 continuously urges the tooth projection 104 in a radially inwardly direction.

The dog 68 is pivotally secured to the bracket 70 by means of a pivot pin 108 extending through a portion of the dog near an end opposite the tooth 104 and which also extends through a projecting portion 110 of the bracket 70. The spring 106 wraps around the pivot pin 108 and has forwardly extending leg portions which are secured to the pivoting dog member 68 and the cannula 28 by appropriate fastening means 112.

A thumb button 114 is provided on the pivotable dog 68 extending upwardly from a top surface thereof which can be used to manually rotate the dog 68 about the pivot pin to move the tooth portion 104 outwardly.

In operation, the cannula 28 is inserted percutaneously into the knee joint so that the forward end 116 projects into a posterior compartment 118 of the knee which can be distended by the introduction of fluid into that compartment. This compartment can be visualized by means of the arthoscopic probe 24 as described in the paper entitled "Swedish Arthroscopic System" by James S. Mulhollan printed in *Orthopedic Clinics of North America*, April, 1982.

When the cannula 28 is in place, the ring member 52 is moved along the cannula until it is abutted against the exterior portion of the knee joint, in firm contact with the patient's skin. The set screw 60 is then tightened to ensure that the ring member 52 will remain stationary with respect to the cannula. The rod 32 is inserted into the cannula by squeezing together the two arms 92 and 80 and pushing on the thumb button 114 so that the two opposed teeth portions of the ratchet mechanisms 62 are moved radially outwardly to provide sufficient clearance to allow passage of the rod through the cannula. The rod member 32 is inserted until the head portion 34 projects beyond the end 116 of the cannula sufficient to allow the hole 44 to be exposed.

The surgical needle has its tip 120 now passed through the tear 22 in the miniscus 20 and is positioned in the compartment 118 into which the cannula 28 extends. The rod 32 is manipulated so that the tip 120 of the needle 46 passes through the opening 44 in the head portion 34 a sufficient distance as is seen in FIG. 5. With the needle 46 thus grasped by the rod 32, the thumb button 114 and the arms 80, 92 are released so that they are captured in a groove 48 in the rod.

The arms 80, 92 are then slowly manually squeezed together and released as seen in FIG. 4 to provide a ratchet-type drive for withdrawing the rod 32 from the cannula 28. The dog member 68 prevents reverse movement of the rod and the pivoting action of the crank 64 allows the tooth portion 90 of the lever 66 to disengage from one channel and be inserted into the next channel. As the withdrawal of the rod 32 occurs, the needle 46 is bent around the end 116 of the cannula, as seen in FIG. 6 and is thus withdrawn through the cannula a sufficient amount to allow for further withdrawal of the rod and captured needle by means of the handle 36 on the end of the rod.

It has been found that the movable ring member 52 is required to give the ratchet mechanism 62 something to push against so that the tip of the cannula 28 does not move relative to the needle location within the joint as the needle is pulled around an angle out through the cannula. Direct manual pulling force is too violent, the ratchet mechanism allows the withdrawal of the needle to occur under control and slowly.

In some presently available surgical systems, a double needle is used in which the suture material extends between the two needles. If such a system is utilized, a rod head 34A as shown in FIG. 8 can be utilized which has two holes 44A passing therethrough to allow for the grasping of both needles at the same time. In all other respects, the construction of this alternate embodiment is identical to that described above.

When two needles are utilized, when they are withdrawn from the cannula, the suture material will extend through the tear in the tissue in two places and both ends of the suture material will be excessible to allow for tying of knots as described in our copending patent application Ser. No. 551,038. When a single needle is utilized, a suture manipulator, comprising a small rod with a hook on the end, captures the loose end of the suture material and carries it to the back of the knee into the compartment 118 where it can be grasped by a currently available instrument and withdrawn through the cannula so that both loose ends of the suture material will be excessible for the physician to tie and set knots.

Thus, it is seen that there is provided by the present invention a needle extractor device which can be used to grasp and extract surgical needles from a relatively inaccessible location without causing the needles to pass entirely through other tissue which may be damaged by the passage of the needles during an operation.

As is apparent from the foregoing specification, the invention is susceptible of being embodied with various alterations and modifications which may differ particularly from those that have been described in the preceeding specification and description. It should be understood that we wish to embody within the scope of the patent warranted hereon all such modifications as reasonably and properly come within the scope of our contribution to the art.

We claim as our invention:

1. A surgical needle extractor for use in extracting elongated surgical needles from a remote, inaccessible location within a patient's body, comprising:
    means for grasping the tip end of the surgical needle at said remote, inaccessible location comprising a rod member having at least one lateral hole passing through said rod near one end thereof,
    means for guiding said grasping means to said remote location comprising a cannula extending from an accessible location to said inaccessible location,
    means for bending and withdrawing said needle from said remote location along said guiding means comprising a ratchet mechanism secured to said cannula to engage said rod member after said tip end of said needle is positioned in said lateral hole, with said lateral hole extending beyond an end of said cannula at said inaccessible location, said engagement of said ratchet mechanism operable to extract said rod member from said cannula and to move said lateral hole to a position immediately adjacent an end of said cannula at said accessible location, and a ring member selectively movably securable to said cannula abuttable against the skin of the patient.

2. The device of claim 1 wherein said rod member has two adjacent lateral holes therethrough.

3. A needle extractor comprising:
    an elongated cannula member with a first end insertable into a patient's body to a remote, inaccessible location and a second end remaining in an accessible location,
    a ring member selectively movable securable to said cannula positionable against the skin of the patient,
    a rod member sized to pass through said cannula and being sufficiently long to extend beyond both ends of said cannula,
        said rod member having a plurality of equally spaced annular channels formed on an exterior surface thereof and having an end with at least one lateral hole passing therethrough,
    a ratchet mechanism secured to said cannula to engage with said channels in said rod member to cause withdrawal of said rod member from said cannula and also to cause movement of said hole in said rod member to a position immediately adjacent said second end when said ratchet mechanism is manually operated.

4. The device of claim 3 wherein said rod member has two holes passing therethrough.

5. A method of extracting an elongated surgical needle from a remote and inaccessible location within a patient's body comprising the steps:
    establishing visual contact with the area of the tip of the needle,
    inserting a cannula into the area where the needle tip is located,
    guiding a needle extractor through said cannula to said remote location,
    grasping said needle tip with said needle extractor,
    bending said needle around the end of said cannula, withdrawing said needle extractor and said needle from said cannula.

* * * * *